United States Patent [19]

Lewis

[11] Patent Number: 4,496,521

[45] Date of Patent: Jan. 29, 1985

[54] INSULIN-POTENTIATING PEPTIDES

[75] Inventor: U. James Lewis, La Jolla, Calif.

[73] Assignee: The Whittier Institute for Diabetes and Endocrinology, La Jolla, Calif.

[21] Appl. No.: 514,158

[22] Filed: Jul. 15, 1983

[51] Int. Cl.³ ..................... A61K 37/00; C07C 103/52
[52] U.S. Cl. .................................. 514/12; 260/112.5 R
[58] Field of Search .................. 424/177; 260/112.5 R

[56] References Cited

PUBLICATIONS

Biol. Abstr. vol. 71, (1981) 73108.
Biol. Abstr. vol. 66, (1978) 51517.
Biol. Abstr. vol. 67, (1979) 45020.
Biol. Abstr. vol. 68, (1979) 47102.
Biol. Abstr. vol. 66, (1978) 70048.
Biol. Abstr. vol. 70, (1980) 77740.
Biol. Abstr. vol. 70, (1980) 4531.

Primary Examiner—Delbert R. Phillips
Assistant Examiner—Delbert R. Phillips

Attorney, Agent, or Firm—Fitch, Even, Tabin & Flannery

[57] ABSTRACT hGH(1-43) having the formula: H—Phe—Pro—Thr—Ile—Pro—Leu—Ser—Arg—Leu—Phe—Asp—Asn—Ala—Met—Leu—Arg—Ala—His—Arg—Leu—His—Gln—Leu—Ala—Phe—Asp—Thr—Try—Gln—Glu—Phe—Glu—Glu—Ala—Try—Ile—Pro—Lys—Glu—Gln—Lys—Tyr—Ser—OH has been found to have remarkable insulin-potentiating action, as has the fragment hGH (17-43). Pharmaceutical compositions in accordance with the invention include hGH(1-43), hGH(17-43) or a biologically active intermediate fragment, or a nontoxic salt thereof, dispersed in a pharmaceutically acceptable carrier. Such peptides or pharmaceutically acceptable salts thereof may be administered to mammals to promote the action of insulin.

Such a peptide can be synthesized by exclusively solid-phase techniques, by partial solid-phase techniques, by fragment condensation, by classical solution addition or by recently developed recombinant DNA techniques.

13 Claims, No Drawings

INSULIN-POTENTIATING PEPTIDES

This invention was made with Government support under grant AM-31416 awarded by DHHS(NIH). The Government has certain rights in this invention.

This invention is generally directed to the field of insulin and human growth hormone. More specifically, the invention relates to fragments of human growth hormone which have been found to have remarkable insulin-potentiating activity.

BACKGROUND OF THE INVENTION

Insulin is a hormone which allows the liver and other organs to store sugar in the form of glycogen and which also controls the oxidation of sugar within the body of mammals. In diabetic subjects, exercise decreases the requirement for insulin. In normal subjects, acute exercise causes insulinopenia and marked increase of muscle glucose utilization. An increased sensitivity of muscle to insulin during exercise has therefore been postulated. During acute exercise, serum levels of radioimmunoassayable growth hormone(GH) are increased severalfold. Since in vivo administration of GH promotes glucose utilization in rats (insulin-like activity), there is the possibility that the hormone or a fragment of the hormone is involved in the increased sensitivity of muscle to insulin. During a study of the early insulin-like action of human GH, it was observed that the fragment corresponding to amino acid residues 32–46 of the molecule could improve the glucose tolerance in mice (L. G. Frigeri et al., 64th Annual Meeting of the Endocrine Society, Abstract #88).

SUMMARY OF THE INVENTION

A 5,000 Dalton fragment of human growth hormone (hGH) was isolated from clinical growth hormone preparation. Analysis of the fragment showed it to be residues 1–43 of hGH, hereafter termed hGH(1–43), having the following amino acid sequence: Phe—Pro—Thr—Ile—Pro—Leu—Ser—Arg—Leu—Phe—Asp—Asn—Ala—Met—Leu—Arg—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser. A second fragment which was similarly isolated was found to be hGH(17–43), having the amino acid sequence: Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser.

It has been found that these peptides have remarkable insulin-potentiating action. Pharmaceutical compositions in accordance with the invention include hGH(1–43) or the fragment hGH(17–43) or a biologically active fragment of intermediate length, or a nontoxic salt of the foregoing, dispersed in a pharmaceutically acceptable carrier. Such peptides or pharmaceutically acceptable salts thereof may be administered to mammals to promote the action of insulin.

DETAILED DESCRIPTION OF THE PREFERRED EMBODIMENTS

The nomenclature used to define the peptides is that specified by Schroeder and Lubke, "The Peptides", Academic Press (1965) wherein, in accordance with conventional representation, the N-terminus appears to the left and the C-terminus to the right. In respect of the present application, where the amino acid residue has isomeric forms, it is the L-form of the amino acid that is being represented.

The invention provides hGH(1–43) having the following formula: H—Phe—Pro—Thr—Ile—Pro—Leu—Ser—Arg—Leu—Phe—Asp—Asn—Ala—Met—Leu—Arg—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser—OH and the fragment hGH(17–43) having the formula: H—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser—OH. The peptide, or a biologically active fragment intermediate length between hGH(1–43) and hGH(17–43), can be synthesized by any suitable method, such as by exclusively solid-phase techniques, by partial solid-phase techniques, by fragment condensation or by classical solution addition. The synthetic peptides may also be produced by recently developed recombinant DNA techniques which may likely be used for large-scale production.

Common to coupling-type chemical syntheses of peptides is the protection of the labile side chain groups of the various amino acid moieties with suitable protecting groups which prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which incudes each of the amino acid residues located in its desired sequence in the peptide chain with various of these residues having side-chain protecting groups.

Also considered to be within the scope of the present invention are intermediates of the formula (II): $X^1$—Phe—Pro—Thr($X^2$)—Ile—Pro—Leu—Ser($X^2$)—Arg($X^3$)—Leu—Phe—Asp($X^4$)—Asn($X^5$)—Ala—Met—Leu—Arg($X^3$)—Ala—His($X^6$)—Arg($X^3$)—Leu—His($X^6$)—Gln($X^5$)—Leu—Ala—Phe—Asp($X^4$)—Thr($X^2$)—Tyr($X^7$)—Gln($X^5$)—Glu($X^4$)—Phe—Glu($X^4$)—Glu($X^4$)—Ala—Tyr($X^7$)—Ile—Pro—Lys($X^8$)—Glu($X^4$)—Gln($X^5$)—Lys($X^8$)—Tyr($X^7$)—Ser($X^2$)—$X^9$, wherein up to 16 amino acid residues can be deleted at the N-terminal, and wherein:

$X^1$ is either hydrogen or an α-amino protecting group. The α-amino protecting groups contemplated by $X^1$ are those known to be useful in the art in the stepwise synthesis of polypeptides. Among the classes of α-amino protecting groups which may be used as $X^1$ are: (1) aromatic urethan-type protecting groups, such as fluorenylmethyloxycarbonyl(FMOC), benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (2) aliphatic urethan protecting groups, such as t-butyloxycarbonyl (BOC), diisopropylmethoxycarbonyl, isopropyloxycarbonyl, ethoxycarbonyl, allyloxycarbonyl; and (3) cycloalkyl urethan-type protecting groups, such as and cyclopentyloxycarbonyl, adamantyloxycarbonyl, and cyclohexyloxycarbonyl. The preferred -amino protecting group is BOC.

$X^2$ is a protecting group for the hydroxyl group of Thr and Ser and is preferably selected from acetyl(Ac), benzoyl(Bz), tert-butyl, triphenylmethyl(trityl), tetrahydropyranyl, benzyl ether(Bzl) and 2,6-dichlorobenzyl(DCB). The most preferred protecting group is Bzl. $X^2$ can be hydrogen, which means there is no protecting group on the hydroxyl group.

$X^3$ is a protecting group for the guanidino group of Arg preferably selected from nitro, p-toluenesulfonyl(Tos), Z, adamantyloxycarbonyl and BOC, or is hydrogen. Tos is most preferred.

$X^4$ is hydrogen or an ester-forming protecting group for the β- or γ-carboxyl group of Asp or Glu, preferably selected from benzyl, 2,6-dichlorobenzyl, methyl, ethyl and t-butyl ester. OBzl is most preferred.

$X^5$ is hydrogen or a protecting group for the amido group of Asn or Gln and is preferably xanthyl(Xan).

$X^6$ is hydrogen or a protecting group for the imidazole nitrogen of His, such as Tos or 2,4-dinitrophenyl(DNP).

$X^7$ is a protecting group for the phenolic hydroxyl group of Tyr, such as benzyl(Bzl), 2,6-dichlorobenzyl(DCB), tetrahydropyranyl, tert-butyl, trityl, Z, substituted Z, e.g. 4Br-Z. DCB is preferred $X^8$ is hydrogen or a protecting group for the ε-amino group of Lys. Illustrative of suitable side chain amino protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore.

Met can optionally be protected by oxygen but is preferably left unprotected.

The selection of a side chain amino protecting group is not critical except that it should be one which is not removed during deprotection of the α-amino groups during the synthesis. Hence, the α-amino protecting group and the side chain amino protecting group cannot be the same.

$X^9$ may be, OH, $OCH_3$, hydrazide, an ester or an ester anchoring bond used in solid phase synthesis for linking to a solid resin support, represented by the formula:

—O—$CH_2$—polystyrene resin support and
—O—$CH_2$—benzyl-polystyrene resin support.

In the Formula (II) for the intermediate, at least one of $X^1$, $X^2$, $X^3$, $X^4$, $X^5$, $X^6$, $X^7$, $X^8$ and $X^9$ is a protecting group or an anchoring bond. Thus, the invention also provides a method for manufacturing a peptide having Formula (I) by (a) first forming a peptide of Formula (II) wherein: $X^1$, $X^2$, $X^3$, $X^4$, $X^5$, $X^6$, $X^7$, and $X^8$, are each either hydrogen or a protective group and $X^9$ is either a protective group or an anchoring bond to resin support or OH, with at least one X-group being either a protecting group or an anchoring bond; (b) splitting off the protective group or groups or anchoring bond from said peptide of Formula (II); and (c) if desired, converting a resulting peptide into a nontoxic salt thereof.

In selecting a particular side chain protecting group to be used in the synthesis of the peptides, the following rules are followed: (a) the protecting group should be stable to the reagent and under the reaction conditions selected for removing the α-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

When the peptides are not prepared using recombinant DNA technology, they are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminal of the peptide by coupling a protected α-amino acid to a suitable resin as generally set forth in U.S. Pat. No. 3,316,891 issued Feb. 23, 1982 to Guillemin et al., the disclosure of which is incorporated herein by reference. Such a starting material for hGH(1–43) can be prepared by attaching α-amino-protected and side chain-hydroxyl-protected Ser to a chloromethylated resin.

Ser protected by BOC and Bzl is coupled to the chloromethylated resin using methylene chloride and dimethylformamide (DMF). Following the coupling of BOC-Ser to the resin support, the α-amino protecting group is removed, as by using trifluoroacetic acid(TFA) in methylene chloride, TFA alone or with HCl in dioxane. Preferably 50 weight % TFA in methylene chloride is used with 0–5 weight % 1,2-ethanedithiol. The deprotection is carried out at a temperature between about 0° C. and room temperature. Other standard cleaving reagents and conditions for removal of specific α-amino protecting groups may be used as described in Schroder & Lubke, "The Peptides", 1 pp 72–75 (Academic Press 1965).

After removal of the α-amino protecting group, the remaining α-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder & Lubke, supra, in Chapter III and by Kapoor, *J. Phar. Sci.*, 59, pp 1–27 (1970).

Each protected amino acid or amino acid sequence is introduced into the solid phase reactor in about a four-fold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp. 1927–1938.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$, $X^7$ and $X^8$ and the α-amino protecting group $X^1$ to obtain the peptide.

The following Example sets forth the preferred method for synthesizing hGH(1-43) by the solid-phase technique.

EXAMPLE I

The synthesis of the hGH(1-43) having the formula: H—Phe—Pro—Thr—Ile—Pro—Leu—Ser—Arg—Leu—Phe—Asp—Asn—Ala—Met—Leu—Arg—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser—OH is conducted in a stepwise manner on a chloromethylated resin, such as available from Lab Systems, Inc., containing about 0.9 meq Cl. The synthesis is performed on an automatic Beckman 990B peptide synthesizer. Coupling of BOC-Ser(Bzl) results in the substitution of about 0.35 mmol. Ser per gram of resin. All solvents that are used are carefully degassed, preferably by sparging with an inert gas, e.g. helium or nitrogen. The program used is generally that reported in Rivier, J. *J. Liquid Chromatogr.*, 1, 343–367 (1978). The procedure set forth by Monahan et al. in *Biopolymers*, 12 (1973) 2513–19 may also be used.

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC—Arg(Tos) is being coupled, a mixture of 50% DMF and methylene chloride is used. Bzl is used as the hydroxyl side-chain protecting group for Ser and Thr. DCB is used to protect the pnenolic hydroxyl group of Tyr. P-nitrophenyl ester(ONp) can be used to activate the carboxyl end of Asn, and for example, BOC—Asn(ONp) is coupled overnight using one equivalent of HOBt in a 50% mixture of DMF and methylene chloride. The amido group of Asn or Gln is protected by Xan when DCC coupling is used instead of the active ester method. 2—Cl—Z is used as the protecting group for the Lys side chain. Tos is used to protect the guanidino group of Arg and the imidazole group of His, and the side chain carboxyl group of Glu or Asp is protected by OBzl. At the end of the synthesis, the following composition is obtained BOC—Phe—Pro—Thr(Bzl)—Ile—Pro—Leu—Ser(Bzl)—Arg(Tos)—Leu—Phe—Asp(OBzl)—Asn(Xan)—Ala—Met—Leu—Arg(Tos)—Ala—His(Tos)—Arg(Tos)—Leu—His(Tos)—Gln(Xan)—Leu—Ala—Phe—Asp(OBzl)—Thr(Bzl)—Tyr(DCB)—Gln(Xan)—Glu(OBzl)—Phe—Glu(OBzl)—Glu(OBzl)—Ala—Tyr(DCB)—Ile—Pro—Lys(2—Cl—Z)—Glu(OBzl)—Gln(Xan)—Lys(2—Cl—Z)—Tyr(DCB)—Ser(Bzl)—resin support. Xan may have been partially or totally removed by TFA treatment used to deblock the α-amino protecting group.

BOC is first removed with 60% TFA in $CH_2Cl_2$. In order to cleave and deprotect the resulting protected peptide-resin, it is treated with 1.5 ml. anisole, 0.5 ml. of methylethylsulfide and 15 ml. hydrogen fluoride(HF) per gram of peptide-resin, first at $-20°$ C. for 20 min. and then at $0.°$ C. for one-half hour. After elimination of the HF under high vacuum, the resin-peptide remainder is washed alternately with dry diethyl ether and chloroform, and the peptide is then extracted with de-gassed 2N aqueous acetic acid and separated from the resin by filtration.

The peptide is then dissolved in 5% acetic acid and subjected to initial purification which may include sephadex G-50 fine gel filtration. The peptide is then further purified by preparative or semi-preparative HPLC, generally as described in Rivier et al., *Peptides: Structure and Biological Function* (1979) pp. 125–128 and Marki et al. *J. Am. Chem. Soc.*, 103, 3178 (1981). The chromatographic fractions are carefully monitored by HPLC, and only the fractions showing substantial purity are pooled.

The fragment hGH(17-43) is synthesized in exactly the same manner by simply terminating the addition of amino acids following the coupling of Ala in the 17-position.

The naturally occurring fragments of human growth hormone hGH(1-43) and hGH(17-43) were found to be common contaminants of impure preparations of hGH which were sufficiently abundant that it was possible to recover about 12 milligrams of hGH(1-43) and about 5 mg. of hGH(17-43) from about 1,000 pituitary glands using techniques as generally previously described by Singh and Lewis, 1981, "Procedure for Isolation of the 2,000 Dalton Variant of Human Growth Hormone", Prep. Biochem., 11, 559-570. The detailed extraction procedure actually employed is set forth in "Human Growth Hormone Peptide 1-43: Isolation from Pituitary Glands", Singh et al., *J. Protein Chem.*, (in press) (1983). Radioimmunoassay showed that the extracted native peptides contained no GH when measured at 1 μg per ml. The absence of GH is also confirmed because the native peptides are inactive at concentrations up to 50 μg per ml. in assays for measuring its ability to stimulate glucose oxidation in adipose tissue from hypophysectomized rats, in which assays purified GH shows that activity at a level of 0.2 ng per ml.

Testing of the peptide with respect to the promotion of the utilization of glucose by the various tissues of mice was measured pursuant to the procedure as set forth in the following Example:

EXAMPLE II

Injections were made intraperitoneally 30 min before administration of a glucose load of 2 mg/g of body weight containing an appropriate amount of (U-$^{14}$C)-D-glucose (Amersham Radiochemicals, Arlington Heights, IN) so that about $8 \times 10^5$ dpm of radiolabeled glucose was given per mouse. Sixty minutes after administration of the mixture, the mice were sacrificed and fragments of liver, diaphragm, and adipose tissue were quickly excised and weighed in a torsion balance. The pieces were placed in vials and digested for 2 hr at 55° C. in 1 molar KOH. After cooling to room temperature, the scintillation liquid was added to the vials. Radioactivity was measured the next day, and an average efficiency of 60% was measured using the internal standard method. Samples of blood were collected at the desired time by intraorbital puncture. Glucose content in the chilled plasma was determined in triplicates by the glucose oxidase method. Blood concentration of radioactive glucose was determined using 20 μl of plasma. Glucose incorporation (GI), expressed in arbitrary units, was calculated by the following equation for the various tissues:

$$GI = \frac{\% \text{ incorporation of } ^{14}\text{C-glucose per g. of tissue } 10^6}{\text{Specific activity of plasma glucose}}$$

The specific activity of plasma glucose is defined as disintegrations per minute of radioactivity×1000 per 100 µl plasma, divided by milligrams of glucose per 100 ml. of plasma. Statistical significance was determined by 1-way analysis of variance and Duncan's multiple range t-test.

Yellow ($A^{vy}/A$) and agouti (A/a) virgin (BALB/c-×VY)F-1 hybrid female mice were produced by mating BALB/c St(rIfC3Hf/Nctr-A/A females by VY/WffC3Hf/Nctr-$A^{vy}$/a males. The mice were housed 3 per 7"×5"×11" polypropylene cage with pine shavings as bedding and fed Wayne Lab Blox (Allied Mills, Inc.) 10% fat diet and tap water ad libitum. Ambient temperature was about 22±1° C., and a 12 hr light cycle was maintained. The results are shown in Table I which follows, which indicates that hGH(1-43) increased the glucose incorporation in the liver by about 100 percent and also increased significantly the incorporation of glucose in adipose tissue. Whereas the effect upon the incorporation of glucose in the diaphragm was of lesser magnitude, it is possible that the values represent the maximal rate of glucose utilization by this muscle. Table IA shows that hGH(17-43) increased glucose incorporation in the liver by close to 35%.

TABLE I

Effect of hGH (1-43) peptide on (U—$^{14}$C)—D-glucose incorporation in VY-F-1 hybrid yellow mice.

| Treatment | | Liver | (%) | Diaphragm | (%) | Adipose Tissue | (%) |
|---|---|---|---|---|---|---|---|
| Saline | (14) | 67.7 ± | — | 44.3 ± | — | 6.45 ± | — |
| | | 2.7 | | 1.5 | | 0.56 | |
| hGH(1-43) (50 µg) | (10) | 135.9 ± 8.2 | 95 | 52.0 ± 2.1* | 17 | 10.5 ± 0.54** | 63 |

The peptide was given 30 min before glucose load.
Data are Mean ± SEM.
The numbers in parentheses indicate number of animals per group.
*<0.05.
**<0.01.

TABLE IA

Effect of hGH(17-43) peptide on (U—$^{14}$C)—D-glucose incorporation in VY-F-1 hybrid yellow mice.

| Treatment | | Liver | (%) |
|---|---|---|---|
| Saline | (5) | 85.6 ± 2.6 | — |
| hGH(1-43) (50 µg) | (5) | 115.2 ± 16 | 35 |

Saline or the peptide was given 30 min before administering a glucose load.
Data are Mean ± SEM.
The numbers in parentheses indicate number of animals per group.

Further testing was carried out on other mice to show the effect of insulin on the utilization of glucose in similar mice. Because the animals were obese and a maximal effect was desired, a large amount of hormone (50 milliunits per mouse) were used. The results are shown in Table II. At this dose, serum glucose levels dropped sharply (Group B), and glucose incorporation of diaphragm and adipose tissue rose compared to the saline-treated control animals (Group A). On the contrary, liver glucose incorporation fell sharply below control levels. Since glucose is stored in liver as glycogen, the data suggests that a depletion of this metabolite from liver occurred. When insulin was given only five minutes prior to the glucose load (Group C) to avoid the serum glucose decrease, the liver glucose incorporation remained unchanged compared to saline-treated control animals—whereas, incorporation in diaphragm and adipose tissue rose to values similar to those observed in the −30 minute treated group (Group B). The action of hGH(1-43) is therefore similar to insulin in its ability to promote glucose utilization, but since the peptide has no direct effect on tissue, its action may be used to potentiate insulin-stimulated glucose uptake as no significant decrease of plasma glucose was observed after administration of hGH(1-43).

TABLE II

Effect of insulin on glucose incorporation of VY-F-1 hybrid yellow mice.

| Plasma Glucose (mg/dl) | | | Glucose Incorporation (arbitrary units/g of tissue) | | |
|---|---|---|---|---|---|
| | | | Liver | Diaphragm | Adipose Tissue |
| A | | | A | | |
| −30 min 141 ± 2.8 | 0 min 150 ± 4.6 | 60 min 338 ± 27 | (14) 67.7 ± 1.5 | 44.3 ± 1.5 | 6.45 ± 0.56 |
| B | | | B | | |
| −30 min 122 ± 2.8 | 0 min 70 ± 8.3 | 60 min 182 ± 11.8 | (8) 36.6 ± 2.6* | 54.4 ± 2.8 NS | 9.1 ± 0.82 NS |
| C | | | C | | |
| −5 min 129 ± 6.5 | 0 min 151. ± 9.5 | 60 min 270 ± 31 | (4) 64.4 ± 9.5 | 52.2 ± 2.4 | 9.0 ± 1.05 |

Insulin was 50 mU per mouse.
Data are Mean ± SEM.
The numbers in parentheses indicate number of animals per group.
*P = 0.0057.
NS = Not Significant when compared with data from line C.
A = Saline
B = Insulin 30 min before glucose load
C = Insulin 5 min before glucose load The data of insulin action on utilization of glucose by the obese mice (Table II) is of help in the understanding of the insulin-like activity of growth hormone fragments. The decrease of glucose incorporation in the liver of mice treated with insulin 30 minutes prior to the administration of a glucose load indicates that glucose is actively released from the organ. This release could be due to glucagon-mediated glycogen breakdown in response both to hypoglycemia and to the abrupt rise of serum exogenous insulin. Involvement of glucagon or other glycolytic hormones on liver glucose release is suggested by the fact that, in diaphragm and adipose tissue which are not affected by glucagon, the incorporation is increased as Table II, Group B shows. When insulin is given only 5 minutes prior to the glucose load to avoid hypoglycemia, the decrease in liver glucose incorporation is not observed. However, although the administration of insulin increased glucose incorporation in diaphragm and adipose tissue, no increase was observed in liver compared to saline-treated animals. This may suggest that some glucagon release subsequent to insulin administration may be counteracting the action of the latter hormone.

The mechanism of action of the hGH peptide is still unknown. A difference from insulin is that the peptide does not stimulate in vitro glucose oxidation in adipose tissue, yet it promotes utilization of U-$^{14}$C glucose when administered in vivo. When the peptide is given together with insulin, an increase of its hypoglycemic activity is observed, suggesting that it can potentiate the action of the hormone. As a result, hGH(1-43) is considered to be particularly valuable for the treatment of mammals, particularly humans, experiencing insulin-deficiency problems. Patients experiencing lower than normal insulin levels may be aided by the administration of such a synthetic peptide which will potentiate the action of native insulin within the body itself. On the other hand, patients experiencing either no or very low insulin levels can be treated by the administration of a combination of insulin, plus such a synthetic peptide, which should permit use of lower than normal insulin dosages.

Thus, hGH(1-43) or hGH(17-43) or a nontoxic salt thereof, combined with a pharmaceutically acceptable carrier to form a pharmaceutical composition, may be administered to mammals, including humans, either intravenously, subcutaneously, intramuscularly or percutaneously, e.g. intranasally. The peptide should be at least about 90% pure and preferably should have a purity of at least about 98%. However, far lower purities would still be substantially greater than the purity of the naturally occurring compound and would effect biological responses. This purity means that the intended peptide constitutes the stated weight % of all like peptides and peptide fragments present. Administration should be prescribed by a physician, and the dosage will vary with the particular condition being treated.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like.

The peptides should be administered under the guidance of a physician, and pharmaceutical compositions will usually contain the peptide in conjunction with a conventional, pharmaceutically-acceptable carrier. The dosage may be from about 1 to about 200 micrograms of the peptide per kilogram of the body weight of the host.

As used herein all temperatures are °C., and all ratios are by volume. Percentages of liquid materials are also by volume.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto. For example, substitutions and modifications at specific positions in the peptide chain might be made without substantially detracting from potency and such peptides are considered as being within the scope of the invention. By consisting essentially of, for purposes of this application, is meant that the peptide is present in substantially greater purity than it is found in any natural extract and that the composition is free from any biologically active substances that would detract from its effectiveness. A fragment of the peptide hGH(1-43) which displays substantially similar biological effectiveness would be considered to be an equivalent of the claimed compound.

Various features of the invention are emphasized in the claims which follow.

What is claimed is:

1. A composition of matter in the form of a synthetic peptide having the formula: H—Phe—Pro—Thr—Ile—Pro—Leu—Ser—Arg—Leu—Phe—Asp—Asn—Ala—Met—Leu—Arg—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser—OH wherein one or more residues can be deleted beginning at the N-terminus and extending through Arg in the 16-position, or a nontoxic salt thereof.

2. A composition in accordance with claim 1 having the formula: H—Phe—Pro—Thr—Ile—Pro—Leu—Ser—Arg—Leu—Phe—Asp—Asn—Ala—Met—Leu—Arg—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser—OH.

3. A composition in accordance with claim 1 having the formula: H—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser—OH.

4. A pharmaceutical composition for potentiating the action of insulin in mammals which composition comprises an effective amount of a peptide having the formula: H—Phe—Pro—Thr—Ile—Pro—Leu—Ser—Arg—Leu—Phe—Asp—Asn—Ala—Met—Leu—Arg—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser—OH wherein one or more residues can be deleted beginning at the N-terminus and extending through Arg in the 16-position, or a nontoxic salt thereof; and a pharmaceutically acceptable carrier therefor.

5. A pharmaceutical composition in accordance with claim 4 in combination with an effective amount of insulin.

6. A composition in accordance with claim 4 wherein said peptide has the formula: H—Phe—Pro—Thr—Ile—Pro—Leu—Ser—Arg—Leu—Phe—Asp—Asn—Ala—Met—Leu—Arg—Ala—His—Arg—Leu—His—Gln—Leu—Ala—Phe—Asp—

Thr—Tyr—Gln—Glu—Phe—Glu—Glu—Ala—Tyr—Ile—Pro—Lys—Glu—Gln—Lys—Tyr—Ser—OH.

7. A composition in accordance with claim 4 wherein said peptide has the formula: H—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser—OH.

8. A method for controlling the oxidation of sugar in mammals and the storage of sugar in the form of glycogen, which method comprises administering to said mammal an effective amount of a peptide having the formula: H—Phe—Pro—Thr—Ile—Pro—Leu—Ser—Arg—Leu—Phe—Asp—Asn—Ala—Met—Leu—Arg—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser—OH wherein one or more residues can be deleted beginning at the N-terminus and extending through Arg in the 16-position or a biologically active N-terminal fragment thereof, or a nontoxic salt thereof.

9. The method in accordance with claim 8 wherein the peptide has the formula: H—Phe—Pro—Thr—Ile—Pro—Leu—Ser—Arg—Leu—Phe—Asp—Asn—Ala—Met—Leu—Arg—Ala—His—Arg—Leu—His—Gln—Leu—Ala—Phe—Asp—Thr—Tyr—Gln—Glu—Phe—Glu—Glu—Ala—Tyr—Ile—Pro—Lys—Glu—Gln—Lys—Tyr—Ser—OH.

10. The method in accordance with claim 8 wherein the peptide has the formula: H—Ala—His—Arg—Leu—His—Gln—Leu—Ala—Phe—Asp—Thr—Try—Gln—Glu—Phe—Glu—Glu—Ala—Tyr—Ile—Pro—Lys—Glu—Gln—Lys—Tyr—Ser—OH.

11. The method in accordance with claim 8 wherein said administering is carried out intravenously, subcutaneously, percutaneously or intramuscularly.

12. The method of claim 11 wherein said administration is at a level between about 1 and about 200 micrograms per kilogram of body weight.

13. The method in accordance with claim 11 wherein said administration is carried out in combination with the administration of an effective amount of insulin.

* * * * *

UNITED STATES PATENT AND TRADEMARK OFFICE
CERTIFICATE OF CORRECTION

PATENT NO. : 4,496,521
DATED : January 29, 1985
INVENTOR(S) : U. James Lewis

It is certified that error appears in the above-identified patent and that said Letters Patent is hereby corrected as shown below:

In the ABSTRACT, Line 5, "Try", both instances should be --Tyr--.

Column 3, Line 26, Insert a period (.) after "preferred".

Column 7, Line 63, after "8.2", insert --**--.

Column 12, Line 14, change "Try" to --Tyr--.

Signed and Sealed this

Fifteenth Day of October 1985

[SEAL]

Attest:

Attesting Officer

DONALD J. QUIGG

Commissioner of Patents and
Trademarks—Designate